US008039816B2

(12) United States Patent
Morishita et al.

(10) Patent No.: US 8,039,816 B2
(45) Date of Patent: Oct. 18, 2011

(54) FLUORESCENCE OBSERVATION APPARATUS

(75) Inventors: Koki Morishita, Tokyo (JP); Shinya Matsumoto, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/953,635

(22) Filed: Nov. 24, 2010

(65) Prior Publication Data

US 2011/0068278 A1    Mar. 24, 2011

Related U.S. Application Data

(63) Continuation of application No. PCT/JP2008/060165, filed on Jun. 2, 2008.

(30) Foreign Application Priority Data

Nov. 24, 2006   (JP) .................................. 2006-316571

(51) Int. Cl.
    *G01N 21/64*    (2006.01)
(52) U.S. Cl. .................................... 250/458.1
(58) Field of Classification Search ............... 250/458.1, 250/459.1
    See application file for complete search history.

(56) References Cited

U.S. PATENT DOCUMENTS

2007/0016077 A1    1/2007    Nakaoka et al.

FOREIGN PATENT DOCUMENTS

| JP | HEI 9-308604 | 12/1997 |
|----|----|----|
| JP | 2006-025802 | 2/2006 |
| JP | 2006-187598 | 7/2006 |
| JP | 2008-61969 | 3/2008 |
| JP | 2008061969 A * | 3/2008 |
| JP | 2008-125934 | 6/2008 |

OTHER PUBLICATIONS

International Search Report dated Jul. 1, 2008.

* cited by examiner

*Primary Examiner* — Mark R Gaworecki
(74) *Attorney, Agent, or Firm* — Scully, Scott, Murphy & Presser, P.C.

(57) ABSTRACT

To accurately obtain fluorescence intensity in a variable passband. Provided is a fluorescence observation apparatus including an excitation light source that emits excitation light; a Fabry-Perot resonator including a variable passband in which the wavelength of light that passes therethrough changes with changes in distance between the surfaces of optical members opposing each other with a distance therebetween, a fixed passband in which the wavelength of light that passes therethrough does not change irrespective of changes in the distance between the surfaces, and a transition band therebetween; an excitation-light cut filter that blocks passage of the excitation light; a band cut filter having a cut-off band including the transition band and not including the wavelength of the excitation light; and a photodetector that detects fluorescence that has passed through the Fabry-Perot resonator, the excitation-light cut filter, and the band cut filter.

5 Claims, 9 Drawing Sheets

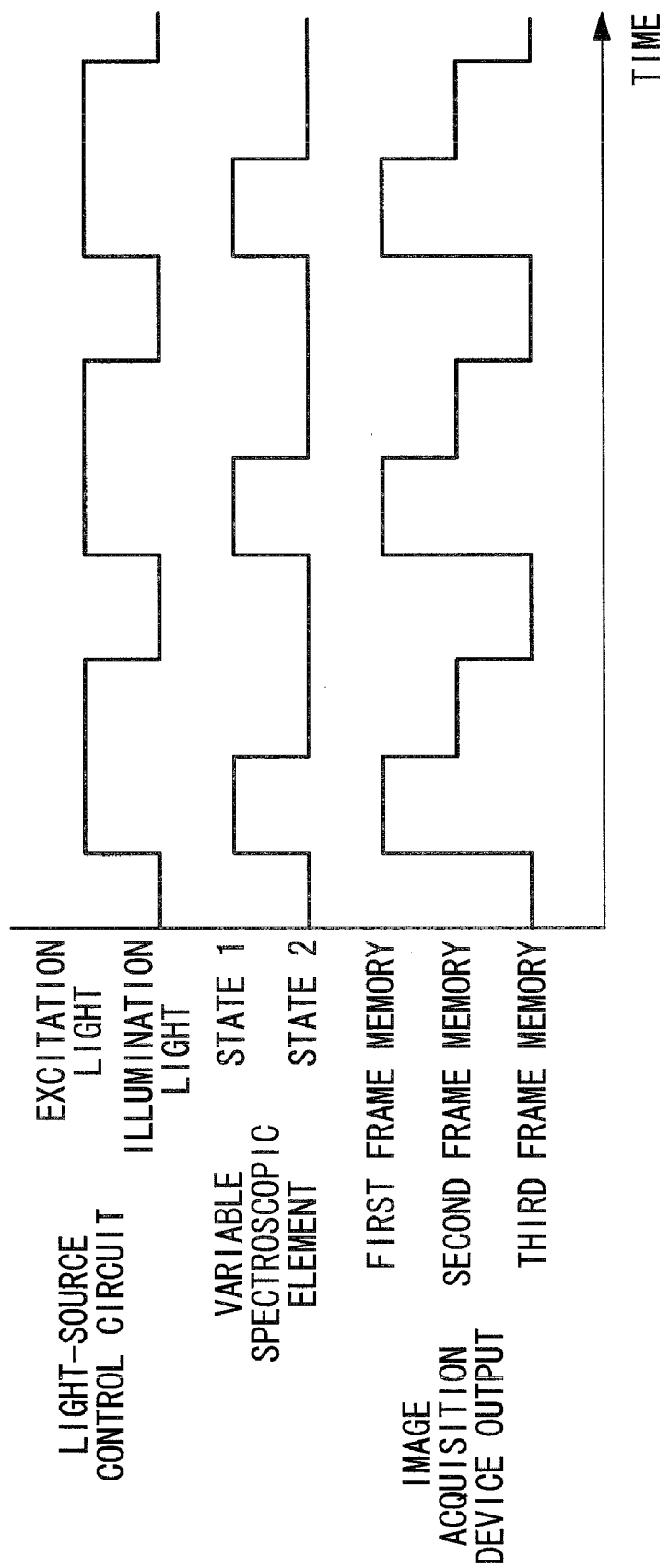

FLUORESCENCE OBSERVATION APPARATUS

CROSS REFERENCE TO RELATED APPLICATIONS

This is a continuation of International Application PCT/JP2008/060165, with an international filing date of Jun. 2, 2008, which is hereby incorporated by reference herein in its entirety.

TECHNICAL FIELD

The present invention relates to a fluorescence observation apparatus.

BACKGROUND ART

A fluorescence endoscope apparatus disclosed in Patent Citation 1 is known as an example of fluorescence observation apparatuses.

In endoscopic observation, observing an autofluorescence image is useful for diagnosing and observing a lesion because information of tissue different from that in a reflected image can be obtained. Observing autofluorescence, that is, tissue-derived fluorescence, has the advantage that the state of the lesion can be observed based on changes of the tissue.

To perform a diagnosis using autofluorescence, it is preferable to obtain fluorescence in a porphyrin-derived fluorescence region of 630 to 650 nm and fluorescence in a collagen-derived fluorescence region of 450 to 550 nm and to calculate and display the ratio thereof (for example, refer to Patent Citation 2).

Patent Citation 1: Japanese Unexamined Patent Application, Publication No. 2006-187598
Patent Citation 2: Japanese Unexamined Patent Application, Publication No. Hei 9-308604

DISCLOSURE OF INVENTION

In the case of Patent Citation 1, to obtain the fluorescence intensity of a porphyrin-derived fluorescence region using a variable spectroscopic element formed of a Fabry-Perot resonator having a fixed passband and a variable passband, the variable spectroscopic element is adjusted to the following two states, and the calculation is performed on the basis of fluorescence intensities obtained in the individual states.

Specifically, the two states of the variable spectroscopic element are a first state in which the fluorescence of both a first fluorescence region that is mainly a collagen-derived fluorescence component and a second fluorescence region that is mainly a porphyrin-derived fluorescence component is obtained and a second state in which only the fluorescence of the first fluorescence region is obtained. By subtracting the fluorescence intensity obtained in the second state from the fluorescence intensity obtained in the first state, the fluorescence intensity of the second fluorescence region can be obtained.

It is an object of the present invention to provide a fluorescence observation apparatus capable of accurately obtaining the fluorescence intensity in a variable passband.

A first aspect of the present invention is a fluorescence observation apparatus including an excitation light source that emits excitation light;

a Fabry-Perot resonator including a variable passband in which the wavelength of light that passes therethrough changes with changes in distance between surfaces of optical members opposing each other with a distance therebetween, a fixed passband in which the wavelength of light that passes therethrough does not change irrespective of changes in the distance between the surfaces, and a transition band therebetween; an excitation-light cut filter that blocks passage of the excitation light; a band cut filter having a cut-off band including the transition band and not including the wavelength of the excitation light; and a photodetector that detects fluorescence that has passed through the Fabry-Perot resonator, the excitation-light cut filter, and the band cut filter.

In the above aspect, the cut-off band of the band cut filter may be located in a band between the fluorescence peak wavelengths of porphyrin and collagen.

Furthermore, in the above aspect, other band cut filter having a cut-off band may be provided in a long wavelength side band in the variable passband.

Furthermore, in the above configuration, the cut-off band of the other band cut filter may be disposed at the long wavelength side relative to the fluorescence band of porphyrin.

Furthermore, in the above configuration, the cut-off band of the other band cut filter may match the passband of one state in the variable passband.

The present invention offers the advantage that the fluorescence intensity in the variable passband can be accurately obtained.

BRIEF DESCRIPTION OF DRAWINGS

FIG. 4 is a timing chart illustrating the operation of the fluorescence observation apparatus in FIG. 1.

| Explanation of Reference | |
|---|---|
| A: | image acquisition target |
| 1: | fluorescence observation apparatus |
| 9: | excitation-light light source (excitation light source) |
| 12: | excitation-light cut filter |
| 13: | variable spectroscopic element (Fabry-Perot resonator) |
| 13a, 13b: | optical member |
| 14: | image acquisition device (photodetector) |
| 20, 21: | band cut filter |

BEST MODE FOR CARRYING OUT THE INVENTION

First Embodiment

A fluorescence observation apparatus 1 according to a first embodiment of the present invention will be described below with reference to FIGS. 1 to 4.

Figure 1:
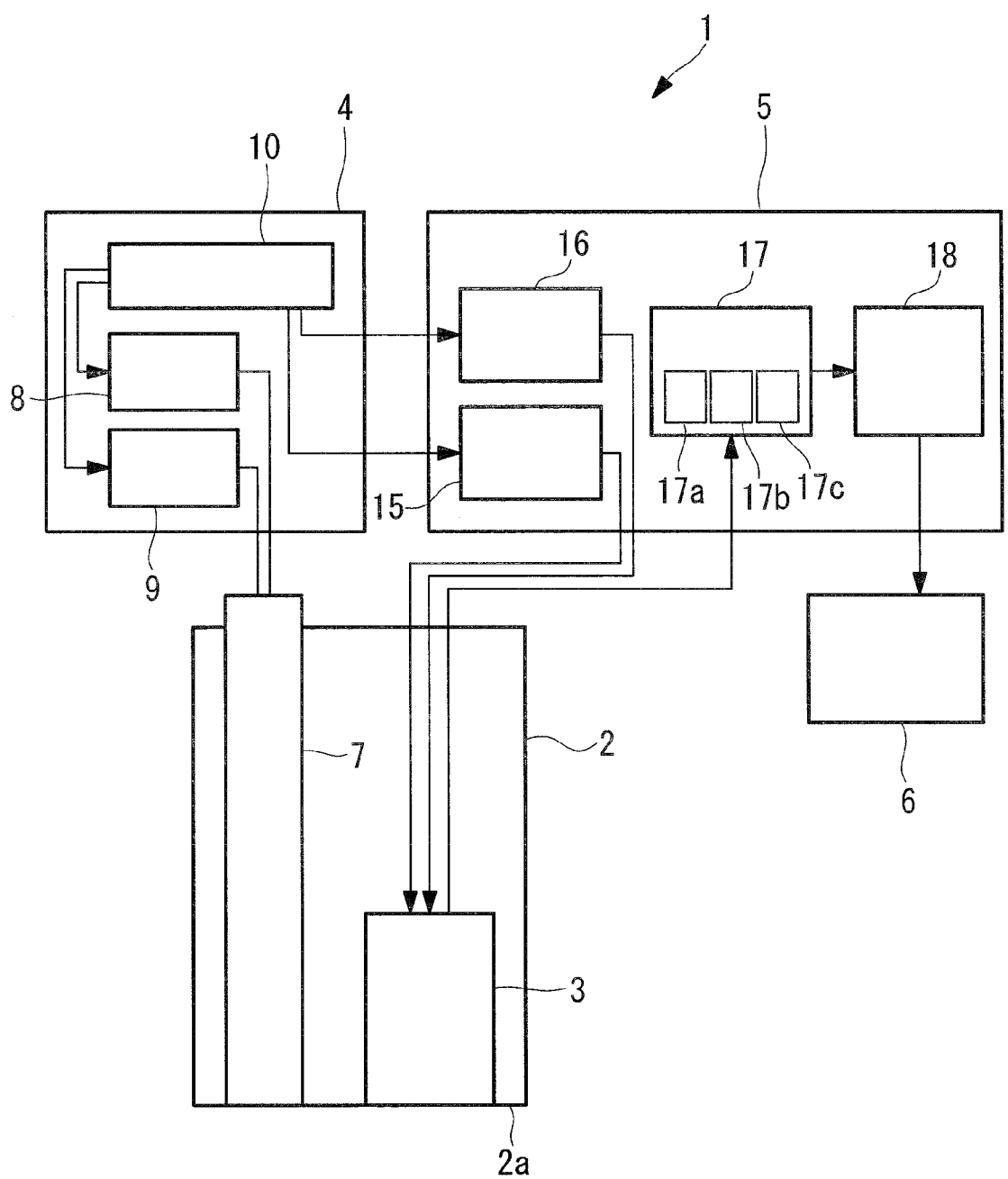
FIG. 1 is a block diagram illustrating the overall configuration of a fluorescence observation apparatus according to a first embodiment of the present invention.

As shown in FIG. 1, the fluorescence observation apparatus 1 according to this embodiment is an endoscopic system provided with an inserted portion 2 to be inserted into a body cavity of a living organism, an image acquisition unit 3 disposed in the inserted portion 2, a light source unit 4 that emits a plurality of kinds of light, a control unit 5 that controls the image acquisition unit 3 and the light source unit 4, and a display unit 6 that displays an image acquired by the image acquisition unit 3.

The inserted portion 2 has an extremely thin outside dimension that allows insertion into a body cavity of a living organism and has, in its interior, a light guide 7 that propagates light from the image acquisition unit 3 and the light source unit 4 to a tip 2a.

The light source unit 4 has an illumination-light light source 8 that emits illumination light for illuminating an observation target in a body cavity and obtaining reflected light that returns upon reflection at the observation target, an excitation-light light source 9 that irradiates an observation target in a body cavity to excite a fluorescence substance present in the observation target, thereby generating fluorescence, and a light-source control circuit 10 that controls these light sources 8 and 9.

The illumination-light light source 8 is a combination of, for example, a xenon lamp and a band-pass filter (not shown), and the 50% passband of the band-pass filter is 450-480 nm. That is, the illumination-light light source 8 is configured to generate illumination light in a wavelength band of 450-480 nm.

Figure 3A:
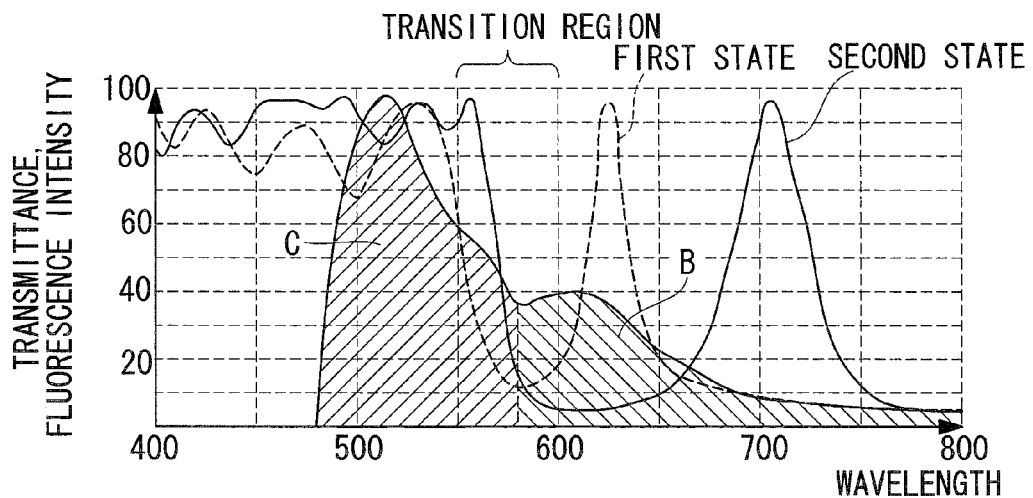
FIG. 3A is a diagram illustrating the transmittance characteristics and the fluorescence wavelength characteristic of a variable spectroscopic element that constitutes the fluorescence observation apparatus in FIG. 1.
Figure 3B:
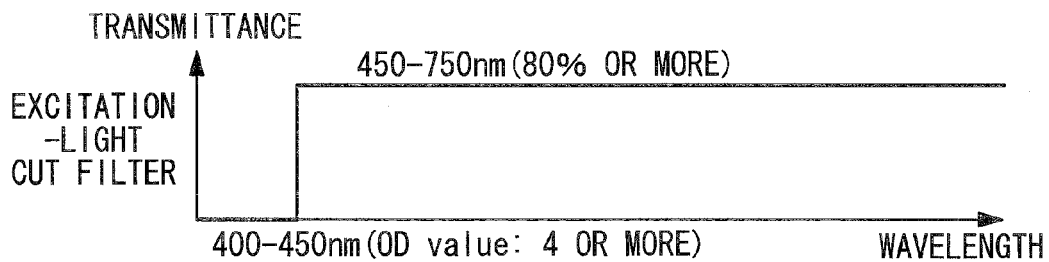
FIG. 3B is a diagram illustrating the transmittance characteristic and the fluorescence wavelength characteristic of an excitation-light cut filter that constitutes the fluorescence observation apparatus in FIG. 1.
Figure 3C:
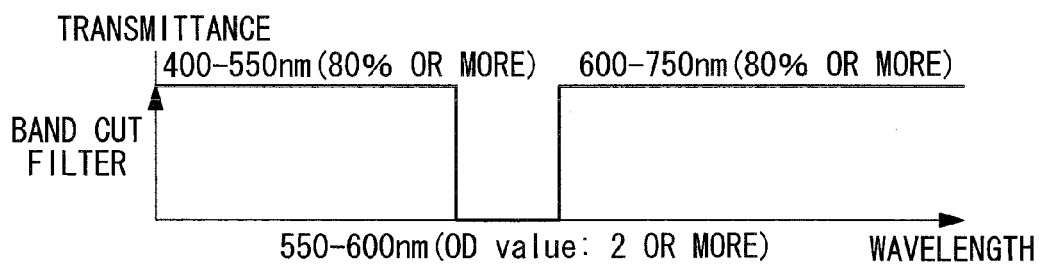
FIG. 3C is a diagram illustrating the transmittance characteristic and the fluorescence wavelength characteristic of a band cut filter that constitutes the fluorescence observation apparatus in FIG. 1.
Figure 3D:
FIG. 3D is a diagram illustrating the transmittance characteristic and the fluorescence wavelength characteristic of a light source for excitation light that constitutes the fluorescence observation apparatus in FIG. 1.

As shown in FIG. 3D, for example, the excitation-light light source 9 is a semiconductor laser that emits excitation light with a peak wavelength of 405±5 nm. The excitation light with this wavelength can excite autofluorescent substances, such as porphyrin and collagen, which are naturally present in living organisms.

The light-source control circuit 10 alternately turns on and off the illumination-light light source 8 and the excitation-light light source 9 at a predetermined timing according to a timing chart described later.

Figure 2:
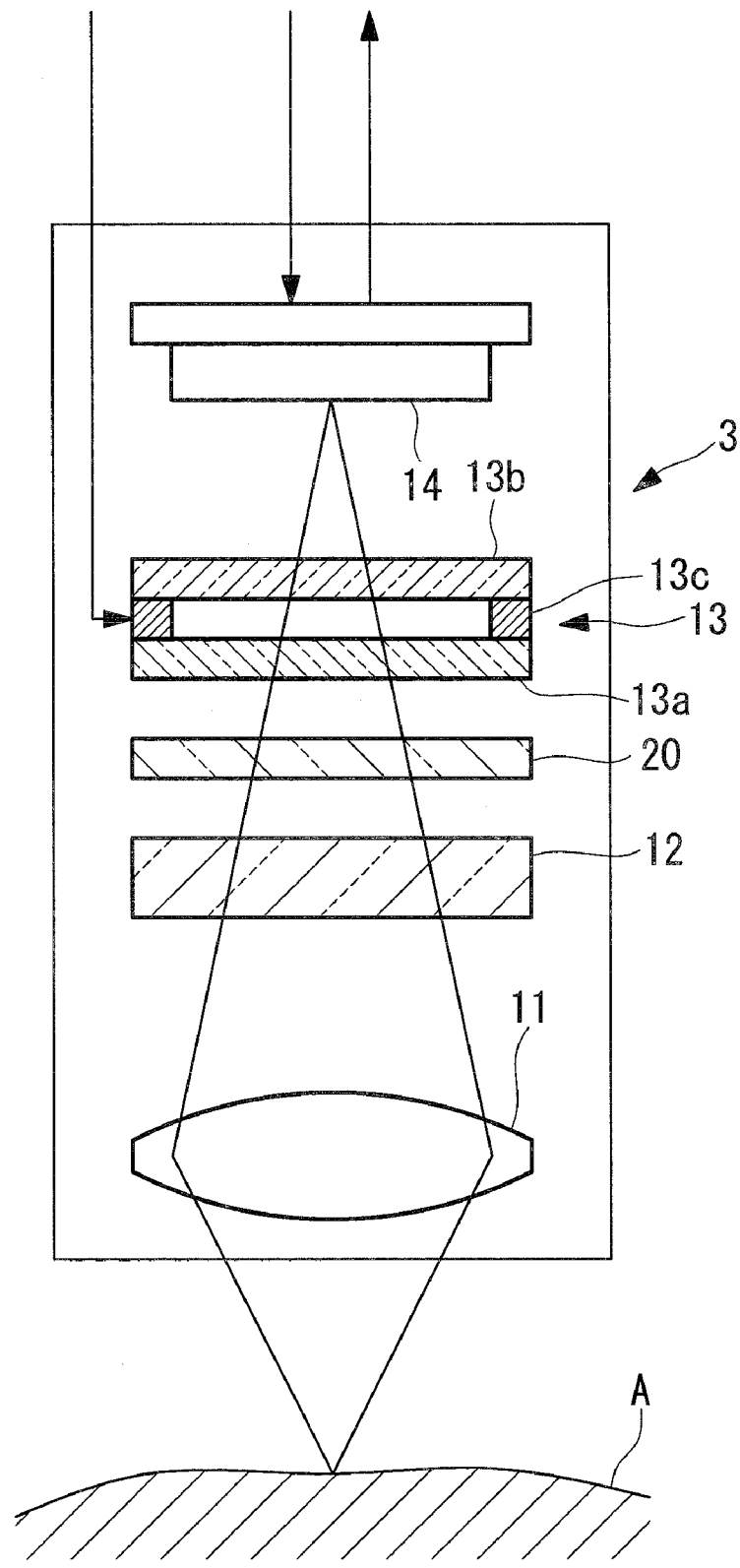
FIG. 2 is a schematic configuration diagram illustrating the internal configuration of an image acquisition unit of the fluorescence observation apparatus in FIG. 1.

As shown in FIG. 2, the image acquisition unit 3 is equipped with an image acquisition optical system 11 that collects light emitted from an observation target A, an excitation-light cut filter 12 that blocks excitation light emitted from the observation target A, a band cut filter 20, a variable spectroscopic element 13 whose spectral characteristics are changed by the operation of the control unit 5, and an image acquisition device 14 that captures the light collected by the image acquisition optical system 11 and converts the light into electrical signals.

The variable spectroscopic element 13 is a Fabry-Perot resonator equipped with two flat optical members 13a and 13b that are disposed in parallel with a space therebetween and that have reflecting films on the opposing surfaces thereof and an actuator 13c that changes the distance between the optical members 13a and 13b. The actuator 13c is, for example, a piezoelectric element. This variable spectroscopic element 13 is configured to change the wavelength band of light that passes therethrough by changing the distance between the optical members 13a and 13b by the operation of the actuator 13c.

More specifically, the variable spectroscopic element 13 has transmittance-wavelength characteristics as shown in FIG. 3A. The variable spectroscopic element 13 is configured to switch between two states depending on a control signal from the control unit 5. In FIG. 3A, the wavelength characteristic indicated by a solid line and the wavelength characteristic indicated by a broken line individually show wavelength characteristics when the variable spectroscopic element 13 is switched between the two states. FIG. 3A also shows the wavelength characteristic of autofluorescence superimposed thereon.

The first state is a state in which the transmittance of a porphyrin-derived fluorescence region B (620 to 670 nm) in a variable passband is increased to a maximum of 50% or more to allow porphyrin-derived fluorescence to pass therethrough. The second state is a state in which the transmittance of the fluorescence region is decreased to 20% or less by moving the passband with a maximum transmittance of 50% or more to a long wavelength side, thereby cutting off the fluorescence of the fluorescence region B.

In other words, the variable spectroscopic element 13 has a variable passband whose transmittance changes depending on the state, in a wavelength band of 620-750 nm.

Furthermore, the variable spectroscopic element 13 has a transmittance of 50% or more in a wavelength band of 550 nm or less irrespective of whether it is in the first or the second state.

In other words, the variable spectroscopic element 13 has a fixed passband whose transmittance does not change, in a wavelength band of 550 nm or less, irrespective of its state.

The fixed passband is located in a collagen-derived fluorescence region C (450-550 nm) and is fixed at a transmittance of 60% or more in this wavelength band. Accordingly, the variable spectroscopic element 13 is configured to allow collagen-derived fluorescence to pass therethrough toward the image acquisition device 14 in both the first and second states.

As shown in FIG. 3A, in a transition region (550-600 nm) disposed between the fixed passband and the variable passband, the transmittance characteristic changes depending on changes in the state of the variable spectroscopic element 13. Accordingly, in this embodiment, as shown in FIG. 3C, the band cut filter 20 is set to an OD value of 2 or more (=transmittance $1\times10^{-2}$ or less) in a wavelength band of 550-600 nm.

This allows fluorescence with a wavelength included in the transition region to be blocked by the band cut filter 20 and fluorescence with a wavelength included in the fixed passband and the variable passband to pass through the band cut filter 20 and to be acquired by the image acquisition device 14.

Furthermore, as shown in FIG. 3B, the excitation-light cut filter 12 is set to an OD value of 4 or more (=transmittance $1\times10^{-4}$ or less) in a wavelength band of 400-450 nm and to a transmittance of 80% or more in a wavelength band of 450-750 nm.

Figure 3E:
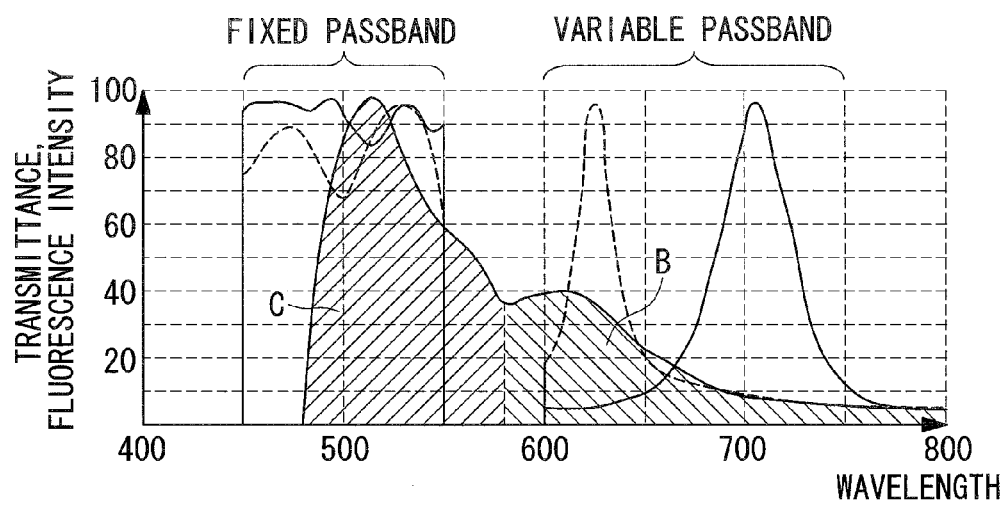
FIG. 3E is a diagram in which the fluorescence wavelength characteristics and the transmittance characteristics and of all of the variable spectroscopic element, the excitation-light cut filter, and the band cut filter that constitute the fluorescence observation apparatus in FIG. 1 are superimposed.

FIG. 3E is a diagram in which the transmittance characteristics and the wavelength characteristics of fluorescence of all of the variable spectroscopic element 13, the excitation-light cut filter 12, and the band cut filter 20 are superimposed.

As shown in FIG. 1, the control unit 5 is equipped with an image-acquisition-device driving circuit 15 that controls driving of the image acquisition device 14, a variable-spectroscopic-element control circuit 16 that controls driving of the variable spectroscopic element 13, a frame memory 17 that stores image information acquired by the image acquisition device 14, and an image processing circuit 18 that processes the image information stored in the frame memory 17 and outputs it to the display unit 6.

The image-acquisition-device driving circuit 15 and the variable-spectroscopic-element control circuit 16 are connected to the light-source control circuit 10 and are configured to control driving of the variable spectroscopic element 13 and the image acquisition device 14 in synchronization with switching of the light-source control circuit 10 between the illumination-light light source 8 and the excitation-light light source 9.

Specifically, as shown in the timing chart in FIG. 4, when excitation light is emitted from the excitation-light light source 9 by the operation of the light-source control circuit 10, the variable-spectroscopic-element control circuit 16 brings the variable spectroscopic element 13 into the first state for a predetermined time to make the image-acquisition-device driving circuit 15 output image information output from the image acquisition device 14 to a first frame memory 17a. Next, the variable-spectroscopic-element control circuit 16 brings the variable spectroscopic element 13 into the second state after the lapse of the predetermined time to make the image-acquisition-device driving circuit 15 output image information output from the image acquisition device 14 to a second frame memory 17b.

Furthermore, when illumination light is emitted from the illumination-light light source 8, the variable-spectroscopic-element control circuit 16 maintains the variable spectroscopic element 13 in the second state, and the image-acquisition-device driving circuit 15 outputs image information output from the image acquisition device 14 to a third frame memory 17c.

Furthermore, the image processing circuit 18 is configured to receive fluorescence image information, obtained by, for example, radiation of excitation light, from the first and second frame memories 17a and 17b, calculate the difference therebetween, and output the obtained differential fluorescence image information to a first channel of the display unit 6 and the fluorescence image information received from the second frame memory 17b to a second channel of the display unit 6, respectively. Furthermore, the image processing circuit 18 is configured to receive reflected-light image information, obtained by radiation of illumination light, from the third frame memory 17c and output it to a third channel of the display unit 6.

The operation of the thus-configured fluorescence observation apparatus 1 according to this embodiment will be described below.

To acquire an image of the image acquisition target A in a body cavity of a living organism using the fluorescence observation apparatus 1 according to this embodiment, the inserted portion 2 is inserted into the body cavity, and the tip 2a thereof is made to face the image acquisition target A in the body cavity. In this state, the light source unit 4 and the control unit 5 are operated to alternately activate the illumination-light light source 8 and the excitation-light light source 9 by the operation of the light-source control circuit 10 to thereby generate illumination light and excitation light, respectively.

The excitation light and illumination light generated in the light source unit 4 are individually propagated to the tip 2a of the inserted portion 2 through the light guide 7 and are radiated from the tip 2a of the inserted portion 2 toward the image acquisition target A.

In the case where excitation light is radiated to the image acquisition target A, an autofluorescent substance, such as porphyrin and collagen, that is naturally present in the image acquisition target A is excited to generate fluorescence. The fluorescence generated by the image acquisition target A is collected by the image acquisition optical system 11 of the image acquisition unit 3, passes through the excitation-light cut filter 12 and the band cut filter 20, and is introduced into the variable spectroscopic element 13.

Since the variable spectroscopic element 13 is first switched to the first state in synchronization with the activation of the excitation-light light source 9 by the operation of the variable-spectroscopic-element control circuit 16, the transmittance for porphyrin-derived fluorescence is increased, thus allowing fluorescence introduced together with the collagen-derived fluorescence to pass therethrough. In this case, part of the excitation light radiated to the image acquisition target A is reflected at the image acquisition target A and is introduced into the image acquisition unit 3 together with the fluorescence; however, since the image acquisition unit 3 is provided with the excitation-light cut filter 12, the excitation light is blocked, thus preventing the excitation light from entering the image acquisition device 14.

Then, the fluorescence that has passed through the variable spectroscopic element 13 is introduced into the image acquisition device 14, and the fluorescence image information is acquired. The acquired fluorescence image information is stored in the first frame memory 17a.

Next, when the variable spectroscopic element 13 is switched to the second state by the operation of the variable-spectroscopic-element control circuit 16, the transmittance for porphyrin-derived fluorescence is reduced, thus allowing only collagen-derived fluorescence to pass therethrough. The fluorescence that has passed through the variable spectroscopic element 13 is introduced into the image acquisition device 14, and the fluorescence image information is acquired. The acquired fluorescence image information is stored in the second frame memory 17b.

The image processing circuit 18 receives the fluorescence image information from the first and second frame memories 17a and 17b and calculates the difference therebetween. Since the first frame memory 17a stores fluorescence image information including both collagen-derived fluorescence and porphyrin-derived fluorescence, and the second frame memory 17b stores fluorescence image information including only collagen-derived fluorescence, fluorescence image information including only the porphyrin-derived fluorescence can be calculated by calculating the difference therebetween.

The calculated fluorescence image information including only the porphyrin-derived fluorescence is output from the image processing circuit 18 to the first channel of the display unit 6, the fluorescence image information including only the collagen-derived fluorescence stored in the second frame memory 17b is output from the image processing circuit 18 to the second channel of the display unit 6, and the fluorescence image information is displayed individually.

In this case, since the fluorescence observation apparatus 1 according to this embodiment is equipped with the band cut filter 20 that blocks light with wavelengths in the transition region between the fixed passband and the variable passband, changes in the transmittance-wavelength characteristic of the variable transition region due to a change in the state of the variable spectroscopic element 13 can be prevented. As a result, this has the advantage that fluorescence image information including only porphyrin-derived fluorescence can be accurately calculated by a difference calculation by means of the image processing circuit 18.

On the other hand, in the case where illumination light is radiated to the image acquisition target A, the illumination light is reflected at the surface of the image acquisition target A, is collected by the image acquisition optical system 11, passes through the excitation-light cut filter 12 and the band cut filter 20, and is introduced into the variable spectroscopic element 13. Since the wavelength band of the reflected light of the illumination light is located in the fixed passband of the variable spectroscopic element 13, all the reflected light introduced into the variable spectroscopic element 13 is allowed to pass through the variable spectroscopic element 13.

Then, the reflected light that has passed through the variable spectroscopic element 13 is introduced into the image acquisition device 14, and the reflected-light image information is acquired. The acquired reflected-light image information is stored in the third frame memory 17c, is output to the third channel of the display unit 6 by the image processing circuit 18, and is displayed by the display unit 6.

Thus, the fluorescence observation apparatus 1 according to this embodiment can provide a user with an image in which two kinds of images, that is, an autofluorescence image derived from an autofluorescent substance and a reflected-light image, are combined.

In this case, since the fluorescence observation apparatus 1 according to this embodiment uses the variable spectroscopic element 13 that changes the transmittance characteristic of light only by changing the distance between the flat optical members 13a and 13b, the very small variable spectroscopic element 13 and image acquisition device 14 can be disposed at the tip 2a of the inserted portion 2. Accordingly, there is no need to extract fluorescence or reflected light from the image acquisition target A and lead it out using a fiber bundle.

Furthermore, in this embodiment, since the state of the variable spectroscopic element 13 is switched in synchronization with switching between the plurality of light sources 8 and 9 in the light source unit 4, images of a plurality of kinds of light having different wavelength bands can be acquired by the same image acquisition device 14. Accordingly, there is no need to provide a plurality of image-capturing optical systems corresponding to fluorescence and reflected light. As a result, the diameter of the inserted portion 2 can be decreased.

It is important to reduce noise when observing particularly faint light such as in fluorescence observation because extraneous light that passes through biological tissues is present even in a body cavity of a living organism; however, since this embodiment can always block light other than light with the wavelength of an observation target, even if the wavelength band thereof changes, by providing the variable spectroscopic element 13 in the image acquisition unit 3, a superior, low-noise image can be acquired.

Furthermore, in this embodiment, the illumination-light light source 8 generates illumination light with a wavelength band of 450-480 nm. Since this wavelength band includes a hemoglobin-absorbing band, information of the structure of blood vessels relatively close to the surface of the living organism etc. can be acquired when an image of light reflected therefrom is acquired.

In the fluorescence observation apparatus 1 according to this embodiment, although the image acquisition unit 3 is configured such that the image acquisition optical system 11, the excitation-light cut filter 12, the band cut filter 20, and the variable spectroscopic element 13 are arranged in this order from the tip 2a side of the inserted portion 2, the arranging order of those components is not limited thereto; any arranging order can be employed.

Figure 5:
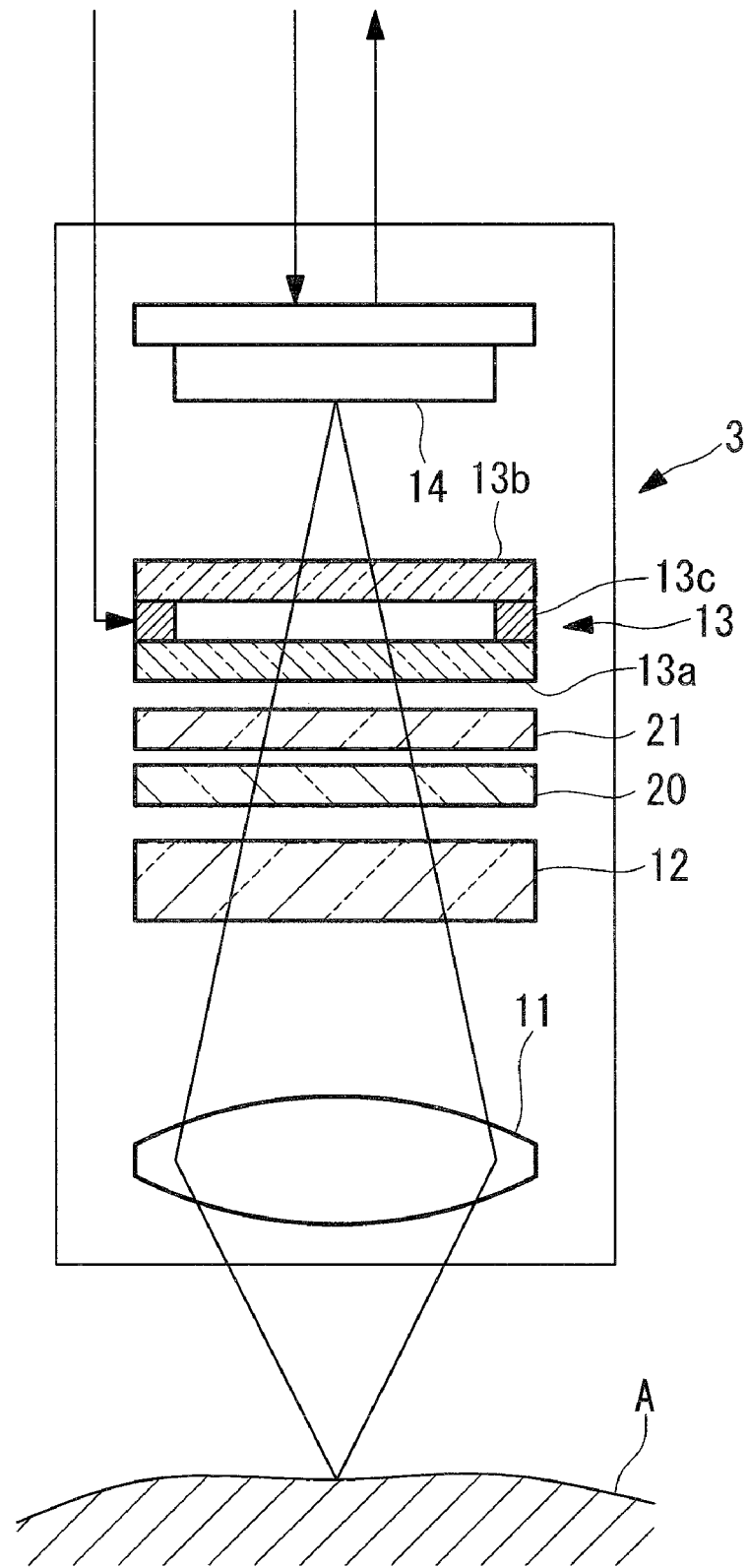
FIG. 5 is a schematic configuration diagram of a modification of the image acquisition unit of the fluorescence observation apparatus in FIG. 1.
Figure 6:
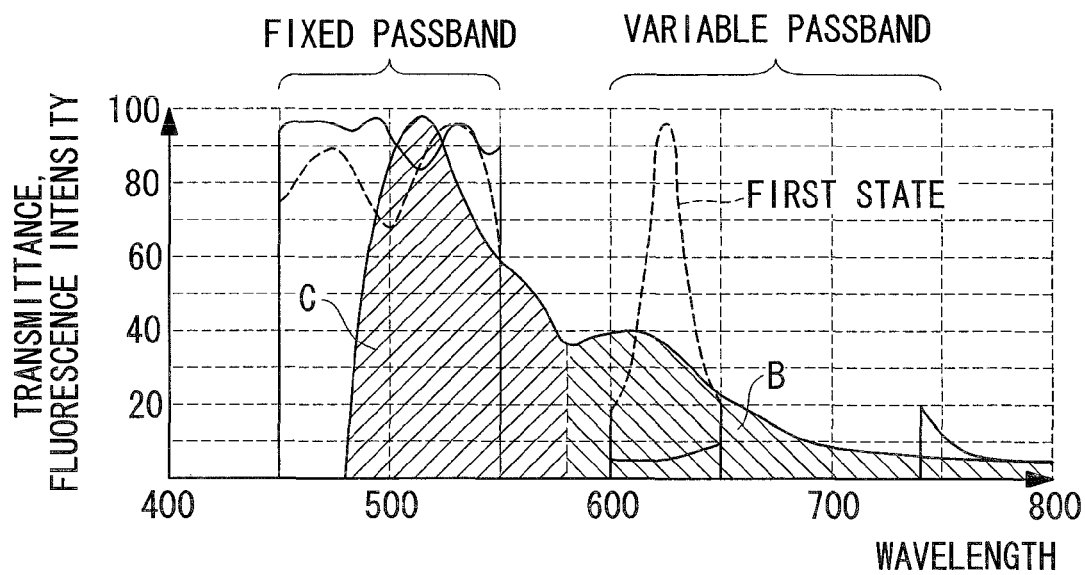
FIG. 6 is a diagram illustrating the transmittance characteristics and the fluorescence wavelength characteristics of all optical components that constitute the fluorescence observation apparatus in FIG. 5.

Furthermore, the fluorescence observation apparatus 1 according to this embodiment uses the band cut filter 20 that blocks light in the transition region between the fixed passband and the variable passband of the variable spectroscopic element 13; in addition, as shown in FIGS. 5 and 6, another band cut filter 21 that blocks light in a wavelength band at the long wavelength side of the variable passband may be provided. For example, one that blocks light with a wavelength band of 650-740 nm is employed as the band cut filter 21.

This can reduce the amount of porphyrin-derived fluorescence to be obtained by the image acquisition device 14, with the variable spectroscopic element 13 in the second state, thus offering the advantage that the difference calculation of the image processing circuit 18 can be performed more accurately.

This further offers the advantage that movement of a high-transmittance region in the variable passband can be minimized.

Instead of the band cut filter 21, a low-pass filter may be employed.

Furthermore, the fluorescence observation apparatus 1 of the present invention is not limited to the scope type that has the image acquisition device 14 at the tip of the inserted portion 2 to be inserted into a body cavity of a living organism and may be applied to a capsule type in which a light source portion, an image acquisition portion, and a variable spectroscopic portion are disposed in one casing, and the whole casing can be inserted into a cavity of a living organism.

More preferably, the configuration of the Fabry-Perot resonator (in which changes in transmittance are small in the fixed passband) of the present invention is as follows.

Second Embodiment

Figure 7:
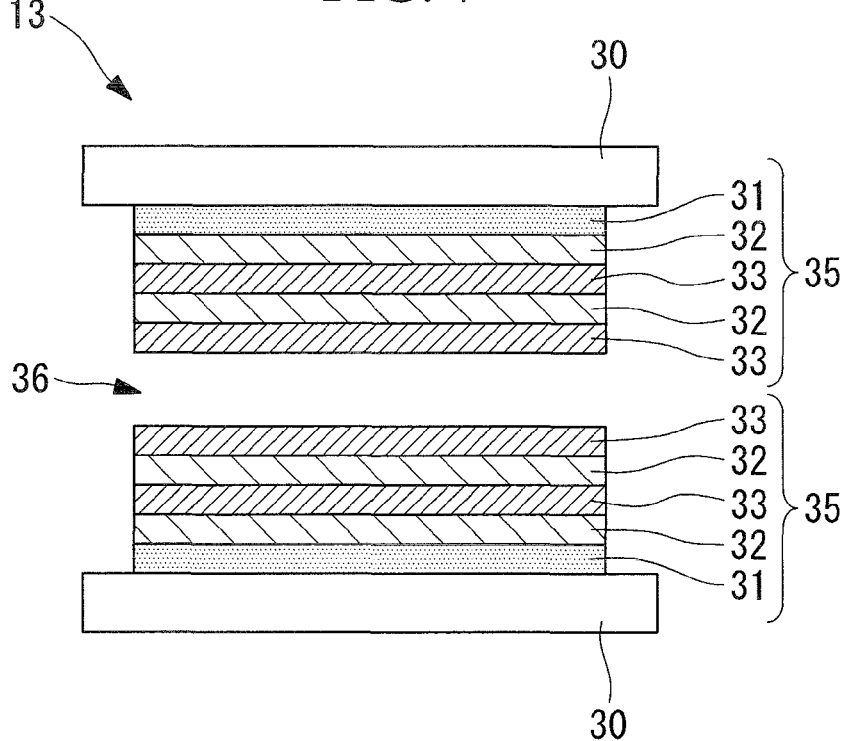
FIG. 7 is a configuration diagram illustrating a Fabry-Perot resonator according to first to fourth embodiments of the present invention.

As shown in FIG. 7, the variable spectroscopic element 13 is constituted by a pair of optical elements. The pair of optical elements is disposed such that multilayer films 35 face each other, with an air layer 36 therebetween. The optical elements are each provided with a substrate 30 made of, for example, quartz, and the multilayer film 35 composed of five layers in total. As shown in Table 1, the multilayer film 35 is stacked in the order from the substrate 30, an $Al_2O_3$ layer 31, a $SiO_2$ layer 32, a $Ta_2O_5$ layer 33, the $SiO_2$ layer 32, and the $Ta_2O_5$ layer 33. The design wavelength λ of the multilayer film 35 is 700 nm.

TABLE 1

| | Film material | Refractive index of material | Optical film thickness (x$\lambda$/4) |
|---|---|---|---|
| Fifth layer | $Ta_2O_5$ | 2.24 | 1.09 |
| Fourth layer | $SiO_2$ | 1.47 | 0.89 |
| Third layer | $Ta_2O_5$ | 2.24 | 1.08 |
| Second layer | $SiO_2$ | 1.47 | 0.95 |
| First layer | $Al_2O_3$ | 1.66 | 0.98 |
| Substrate | Quartz | 1.46 | |

Figure 8:
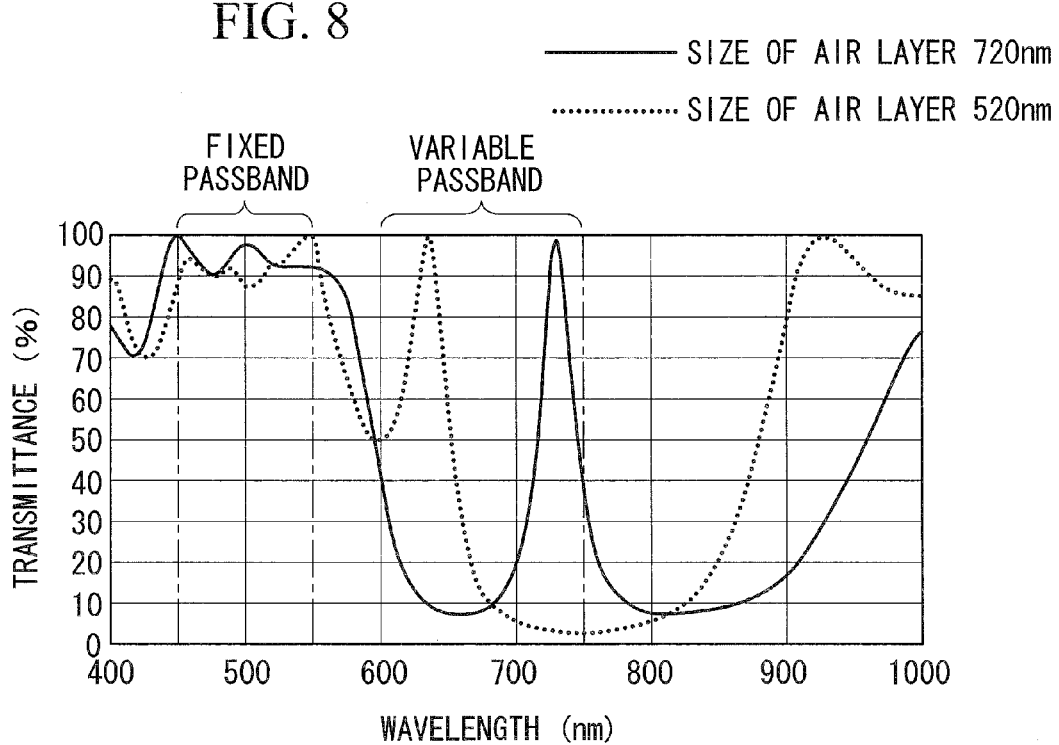
FIG. 8 is a graph illustrating the optical characteristics of the Fabry-Perot resonator according to the second embodiment of the present invention.

The spectral transmittance characteristics of this variable spectroscopic element 13 are shown in FIG. 8. Here, the vertical axis in FIG. 8 indicates transmittance, and the horizontal axis indicates wavelength. A spectral transmittance characteristic in the case where the size of the air layer 36 is 720 nm (a second state) is indicated by a solid line, and a spectral transmittance characteristic in the case where the size of the air layer 36 is 520 nm (a first state) is indicated by a dotted line.

If the size of the air layer 36 changes from 720 nm to 520 nm in the variable spectroscopic element 13, the peak wavelength of the variable passband changes from 730 nm to 630 nm. On the other hand, changes in the transmittance of the fixed passband are small, and the transmittance is substantially constant, with a difference in transmittance of 7% or less.

Using the variable spectroscopic element 13 with the configuration of the multilayer film in Table 1 makes it possible to accurately detect only porphyrin-derived fluorescence.

Third Embodiment

Figure 9:
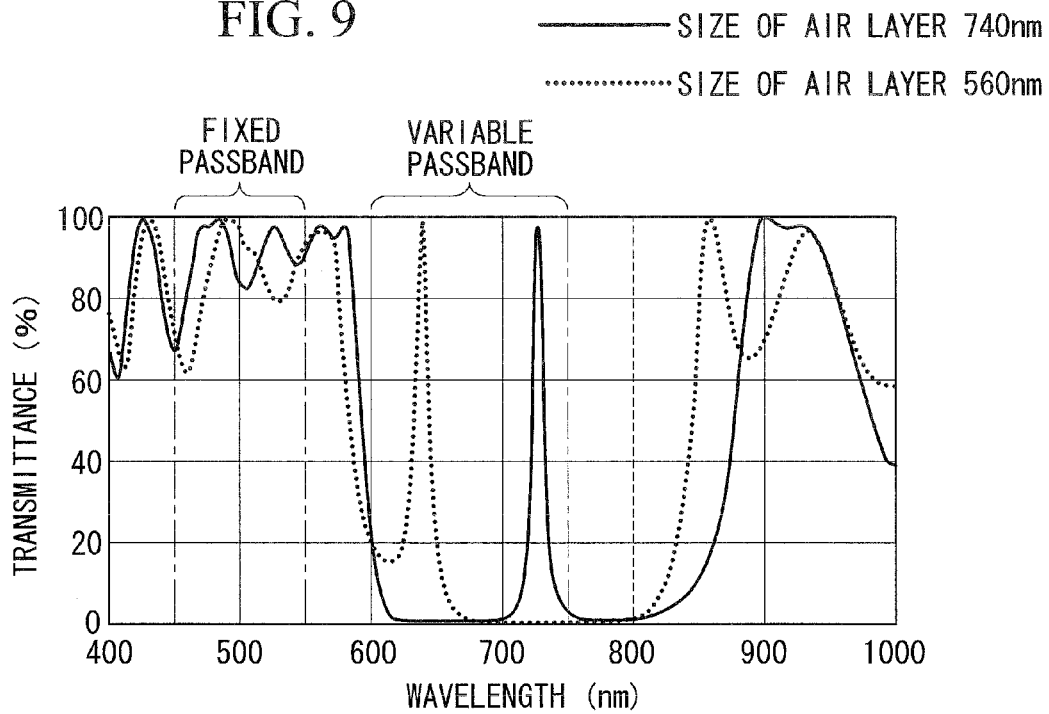
FIG. 9 is a graph illustrating the optical characteristics of the Fabry-Perot resonator according to the third embodiment of the present invention.

Next a third embodiment will be described with reference to FIG. 9.

The same components as in the foregoing second embodiment are given the same reference numerals, and descriptions thereof will be omitted.

Differences between the third embodiment and the second embodiment are that the thickness of the air layer in the variable spectroscopic element 13 changes between 740 nm and 560 nm. Even if the value of the size differs, the peak wavelength is the same as in the first embodiment. That is, also in this embodiment, the peak wavelength in the variable passband changes from 730 nm to 630 nm. Furthermore, changes in the spectral transmittance characteristic in the fixed passband are small; the transmittance is substantially constant, with a difference in transmittance of 10% or less. This is also the same as in the second embodiment.

As shown in Table 2 (design wavelength $\lambda$ is 700 nm), for example, this variable spectroscopic element 13 is provided with multilayer films each composed of seven layers in total, in which a $Ta_2O_5$ layer and a $SiO_2$ layer are alternately stacked from the substrate side, and the multilayer films face each other, with the air layer therebetween.

TABLE 2

| | Film material | Refractive index of material | Optical film thickness (x$\lambda$/4) |
|---|---|---|---|
| Seventh layer | $Ta_2O_5$ | 2.24 | 1.19 |
| Sixth layer | $SiO_2$ | 1.47 | 0.76 |
| Fifth layer | $Ta_2O_5$ | 2.24 | 1.12 |
| Fourth layer | $SiO_2$ | 1.47 | 0.87 |
| Third layer | $Ta_2O_5$ | 2.24 | 1.08 |
| Second layer | $SiO_2$ | 1.47 | 0.97 |
| First layer | $Ta_2O_5$ | 2.24 | 1.15 |
| Substrate | Quartz | 1.46 | |

Using the variable spectroscopic element 13 with the configuration of the multilayer film in Table 2 further narrows the half bandwidth at the peak wavelength in the variable passband, thus also enhancing the wavelength resolution.

Fourth Embodiment

Figure 10:
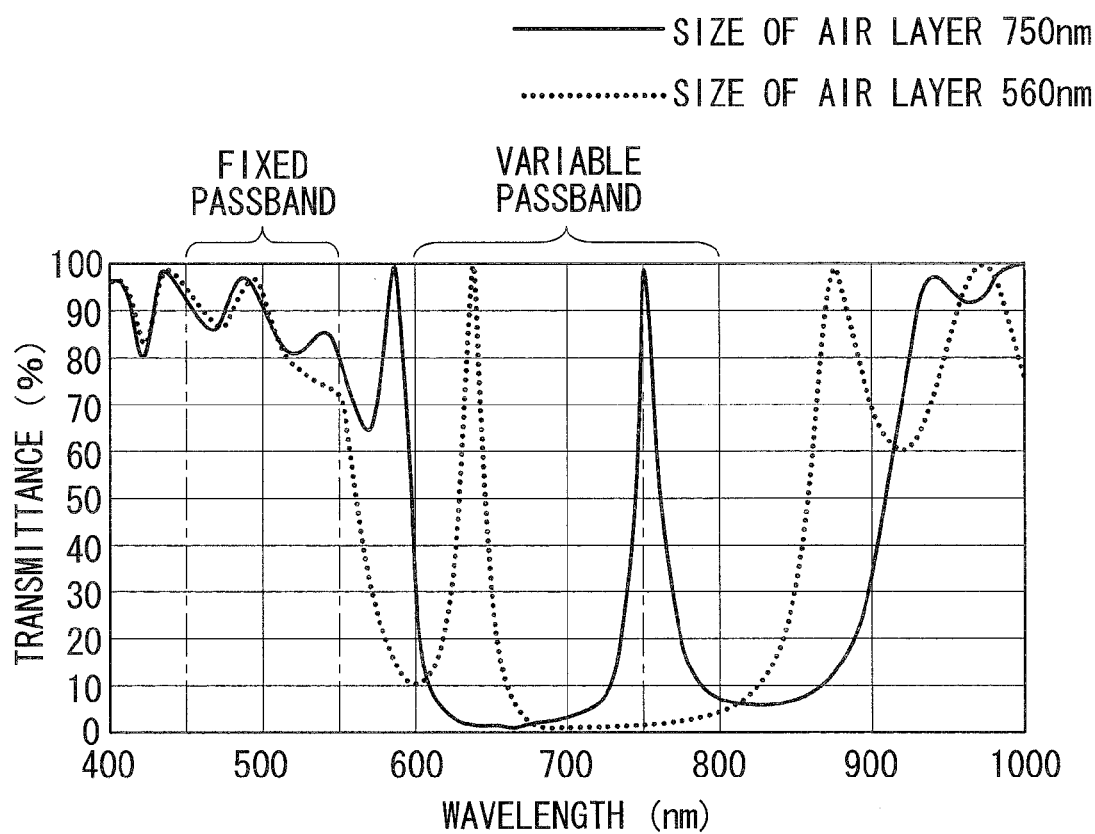
FIG. 10 is a graph illustrating the optical characteristics of the Fabry-Perot resonator according to the fourth embodiment of the present invention.

Next, a fourth embodiment will be described with reference to FIG. 10.

The same components as in the foregoing other embodiments are given the same reference numerals, and descriptions thereof will be omitted.

In this embodiment, the thickness of the air layer 36 of the variable spectroscopic element 13 changes between 750 nm and 560 nm. In this case, as shown in FIG. 10, the peak wavelength in the variable passband changes from 730 nm to 630 nm. Furthermore, changes in the spectral transmittance characteristic in the fixed passband are small; the transmittance is substantially constant, with a difference in transmittance of 3% or less.

As shown in Table 3 (design wavelength $\lambda$ is 700 nm), for example, this variable spectroscopic element 13 is provided with substrates and multilayer films each composed of nine layers in total, in which $Al_2O_3$ layers are disposed on the substrate and at the uppermost layer, and a $Ta_2O_5$ layer and a $SiO_2$ layer are alternately stacked between the $Al_2O_3$ layers, and the multilayer films face each other, with the air layer therebetween.

TABLE 3

| | Film material | Refractive index of material | Optical film thickness (x$\lambda$/4) |
|---|---|---|---|
| Ninth layer | $Al_2O_3$ | 1.66 | 0.28 |
| Eighth layer | $Ta_2O_5$ | 2.24 | 0.93 |
| Seventh layer | $SiO_2$ | 1.47 | 0.88 |
| Sixth layer | $Ta_2O_5$ | 2.24 | 0.96 |
| Fifth layer | $SiO_2$ | 1.47 | 1.00 |
| Fourth layer | $Ta_2O_5$ | 2.24 | 0.96 |
| Third layer | $SiO_2$ | 1.47 | 1.19 |
| Second layer | $Ta_2O_5$ | 2.24 | 1.44 |
| First layer | $Al_2O_3$ | 1.66 | 0.82 |
| Substrate | Quartz | 1.46 | |

The technical scope of the present invention is not limited to the embodiments described above, and various modifications may be made without departing from the spirit of the present invention.

The invention claimed is:

1. A fluorescence observation apparatus comprising:
an excitation light source that emits excitation light;
a Fabry-Perot resonator including a variable passband in which the wavelength of light that passes therethrough changes with changes in distance between surfaces of optical members opposing each other with a distance therebetween, a fixed passband in which the wavelength of light that passes therethrough does not change irrespective of changes in the distance between the surfaces;

an excitation-light cut filter that blocks passage of the excitation light;

a band cut filter having a cut-off band including a transition band between the fixed passband and the variable passband and not including the wavelength of the excitation light; and a photodetector that detects fluorescence that has passed through the Fabry-Perot resonator, the excitation-light cut filter, and the band cut filter.

2. The fluorescence observation apparatus according to claim 1, wherein the cut-off band of the band cut filter is located in a band between the fluorescence peak wavelengths of porphyrin and collagen.

3. The fluorescence observation apparatus according to claim 1, comprising:

other band cut filter having a cut-off band in a long wavelength side band in the variable passband.

4. The fluorescence observation apparatus according to claim 3, wherein the cut-off band of the other band cut filter is disposed at the long wavelength side relative to the fluorescence band of porphyrin.

5. The fluorescence observation apparatus according to claim 3, wherein the cut-off band of the other band cut filter matches the passband of one state in the variable passband.

* * * * *